US012337155B2

(12) United States Patent
Ben David (10) Patent No.: US 12,337,155 B2
(45) Date of Patent: Jun. 24, 2025

(54) LIQUID DELIVERY DEVICE AND METHOD

(71) Applicants: InnoCAT LTD., Givat Ela (IL); Ishai Ben David, Givat Ela (IL)

(72) Inventor: Ishai Ben David, Givat Ela (IL)

(73) Assignee: InnoCAT LTD., Givat Ela (IL)

( * ) Notice: Subject to any disclaimer, the term of this patent is extended or adjusted under 35 U.S.C. 154(b) by 680 days.

(21) Appl. No.: 17/756,232

(22) PCT Filed: Nov. 19, 2020

(86) PCT No.: PCT/IB2020/060926
§ 371 (c)(1),
(2) Date: May 19, 2022

(87) PCT Pub. No.: WO2021/099992
PCT Pub. Date: May 27, 2021

(65) Prior Publication Data
US 2023/0001100 A1 Jan. 5, 2023

Related U.S. Application Data

(60) Provisional application No. 62/938,678, filed on Nov. 21, 2019.

(51) Int. Cl.
*A61M 5/315* (2006.01)
*A61M 5/142* (2006.01)
*A61M 5/145* (2006.01)

(52) U.S. Cl.
CPC .... *A61M 5/31578* (2013.01); *A61M 5/14244* (2013.01); *A61M 5/14546* (2013.01); *A61M 2005/14268* (2013.01); *A61M 2005/3152* (2013.01)

(58) Field of Classification Search
None
See application file for complete search history.

(56) References Cited

U.S. PATENT DOCUMENTS

| 2012/0136306 A1 | 5/2012 | Bartha |
| 2012/0197212 A1 | 8/2012 | Basso et al. |
| 2016/0325041 A1 | 11/2016 | Hoeholt et al. |
| 2019/0366010 A1 | 12/2019 | Cardinali et al. |

FOREIGN PATENT DOCUMENTS

| EP | 1752172 A1 | 8/2005 |
| WO | 2019/076593 A1 | 4/2019 |

OTHER PUBLICATIONS

Extended European Search Report issued in EP Application No. 20889164.8, dated Oct. 23, 2023.
International Search Report and Written Opinion issued for International Application No. PCT/IB2020/060926, mailed Jul. 16, 2021 in 11 pages.

*Primary Examiner* — Manuel A Mendez
(74) *Attorney, Agent, or Firm* — Knobbe, Martens, Olson & Bear, LLP (57) ABSTRACT

A crawling mechanism for a drug delivery device has a central longitudinal axis and is arranged to crawl in an axial direction. The crawling mechanism includes a housing and one or more swing members pivotally coupled to the housing that are arranged to swing relative to the housing between an initial position and a terminal position suitable for urging crawling of the mechanism.

16 Claims, 11 Drawing Sheets

LIQUID DELIVERY DEVICE AND METHOD

CROSS REFERENCES TO RELATED APPLICATIONS

This application is a U.S. national phase entry of, and claims priority to, PCT International Patent Application No. PCT/IB2020/060926, filed Nov. 19, 2020, which claims priority to U.S. Provisional Patent Application No. 62/938,678, filed Nov. 11, 2019.

TECHNICAL FIELD

Embodiments of the invention relate to a liquid e.g. drug or the like delivery device and method, in particular for delivering such liquids/drugs from cartridges.

BACKGROUND

Liquid delivery devices such as drug delivery devices, insulin pumps (or the like) should preferably fulfill various requirements. For example, dosage accuracy is an important parameter that influences the performance of the device and specifically in drug delivery devices is critical to the user's health.

Overall dimensions and weight of such liquid delivery device is another parameter that influences user's experience and specifically in drug delivery devices influences a user's willingness or ability to carry the device.

The cost of goods also influences profitability and ability of a user to purchase such a device, and prefilled cartridge compatibility is another parameter that enables a user to use the device in compatible with a prefilled cartridge.

It is thus advantageous to provide a liquid delivery device that can address at least some parameters such as those mentioned above.

SUMMARY

The following embodiments and aspects thereof are described and illustrated in conjunction with systems, tools and methods which are meant to be exemplary and illustrative, not limiting in scope.

In an aspect of the present disclosure there is provided a device and/or method for delivering liquid substances such drugs, medications, vitamin additives, minerals, chemotherapy or chemo drugs, liquids containing DNA (or the like) out of a container of or associated with the device.

In various embodiments, such container may be a syringe, a cartridge, a pre-filled cartridge (or the like).

Various embodiments of the present disclosure may thus be defined as aimed at providing a suitable solution for provision of dosage accuracy in a relative compact device structure that may be a substantially low cost liquid delivery device, and which can be used to displace substances (liquids, drugs and the like) out of container cartridges and/or prefilled cartridges.

In an embodiment, a liquid delivery device may be arranged to include a crawling mechanism that can be inserted (at least partially) into a cartridge of the device, to engage with a plunger and with an internal peripheral surface of the cartridge.

Such crawling mechanism may be arranged to bear against and urge the plunger to be biased into the interior of the cartridge in order to urge delivery of substances, such as liquid drugs (or the like) out of the container.

In an embodiment, the crawling mechanism may be arranged to include several components, such as a motor and reduction gear, driving wheels and swinging hooks.

In an embodiment, a method for delivering substances such as liquid, drugs (or the like) out of a container of the device may include a setup stage.

Such setup stage may include urging engagement (possibly by a user of the device) between a cartridge and a crawling mechanism of the device.

Such engagement may urge a plunger of the device to come into contact with edges of swinging hooks of the crawling mechanism, which in turn nay be pushed axially and due to swinging points the swinging hooks may then be urged to rotate. Such swinging hooks may be included in swing members of the crawling mechanism.

In an embodiment, the swinging hooks of a swing member may be arranged as a so-called frame, possibly formed of or made to include a pair of side-bars, for driving wheels, which in turn may be forced away from the axis of the cartridge due to such swinging action until they come into contact and engage with an internal peripheral wall/surface of the cartridge.

In an embodiment, axial forces applied to swing members e.g. to tips of the swinging hooks by the plunger, may cause a swinging motion of the swing member and consequently swinging hooks, hence, causing an generally arced (partially radial) motion to the driving wheels associated to such swing members till they come into substantial contact with the internal peripheral wall of the cartridge.

Radial forces between the driving wheels and the internal peripheral wall of the cartridge may urge creation of frictional force between the driving wheels and the internal peripheral wall of the cartridge—resulting in the torque being delivered to the rotation of driving wheels being translated to an axial force, causing the crawling mechanism to move axially.

Due to the swinging motion and the axial force, swinging hooks of swing members may be arranged in certain cases to penetrate into the plunger to thereby complete the setup stage.

In an embodiment, a method for delivering substances such as liquid, drugs (or the like) out of a container of the device may include a subsequent delivery stage that may be activated after the setup stage.

The delivery stage may include activation of a motor possibly coupled with the driving wheels via a gear possibly a reduction gear.

Rotation of the driving wheels in the delivery stage may be performed while the driving wheels are in contact with the internal wall of the cartridge.

Hence, the crawling mechanism in at least certain embodiments may be arranged to move forward inside the cartridge while forcing the plunger to move forward as well, delivering substances out of the cartridge.

A rotation encoder that may be located in association with the motor, possibly at a back of the motor, may assist in controlling/monitoring the rotational motion of the motor.

A linear encoder may be integrated into a cable that delivers power/data from a PCB of the motor, to thereby control/monitor linear motion of the motor/plunger.

In an embodiment, a method for delivering substances such as liquid, drugs (or the like) out of a container of the device may include an additional detachment stage that may be activated after the delivery stage.

The crawling mechanism may be detached from the cartridge by request, either by manually pulling the cartridge away from the crawling mechanism and/or by electrical command to the motor to rotate in the opposite direction of delivery.

Since in some cases the swinging hooks may penetrate into the plunger, manually pulling the cartridge away from the crawling mechanism in such embodiments may result in application of axial forces on the edge of the swinging hooks, causing the swinging hooks to rotate in a counter direction, so that the driving wheels are forced away from the internal wall of the cartridge and towards the axis of the cartridge.

In addition or alternatively, once the disposable part is detached from the reusable part (remainder of device including crawling mechanism), a coupling sensor may trigger the system into a "detachment stage", causing the driving wheels to rotate in a backwards direction to detach the crawling mechanism from the cartridge.

A spring (which possibly applies force to the flex PCB) may be arranged to pull the crawling mechanism to its base position in certain embodiments.

In various embodiments, edges of the swinging hooks may be attached to the plunger by penetrating into it (as described), however in other embodiments such attachment may be accomplished in others means, such as by vacuum cups, adhesive, magnet, etc. In certain embodiments, the swinging hooks may not form attachment with the plunger, but merely close abutting attachment (or the like).

In various embodiments, the crawling mechanism can be powered either by a cable or it may include its own power source (e.g. Battery)

In various embodiments, control signals can be delivered to the crawling mechanism either by cable or by wireless signals.

Further aspects of the present invention are exemplified in the following:
1. A liquid/drug delivery device including a crawling mechanism while one or more of the component of the crawling mechanism is in contact with the internal surface of the cartridge (in at least at one contact area).
2. A plunger driving mechanism which is advancing with the plunger inside a cylindrical, rectangular, arced, oval or other shaped fluid cartridge.
3. A plunger driving mechanism which is advancing a plunger inside a fluid cartridge and wherein the driving mechanism is entirely enclosed inside the cartridge, at least when the cartridge is empty.
4. A plunger driving mechanism which is anchored to the plunger in forward motion and released from the plunger in backward motion.
5. A drug delivering system that includes a linear encoder that monitors the motion of the plunger and an elastic element (spring) that can pull the crawling mechanism back to its base position.
6. A drug delivery system with a coupling sensor between the reusable and the disposable units that can detect attachment/detachment between the reusable and disposable parts.
7. A drug delivery system with a seal that is located around the drug cartridge for ingress protection/sealing.
8. A drug delivery device which uses pre-filled cartridge and is attachable to the human body with an adhesive.

In addition to the exemplary aspects and embodiments described above, further aspects and embodiments will become apparent by reference to the figures and by study of the following detailed descriptions.

BRIEF DESCRIPTION OF THE FIGURES

Exemplary embodiments are illustrated in referenced figures. It is intended that the embodiments and figures disclosed herein are to be considered illustrative, rather than restrictive. The invention, however, both as to organization and method of operation, together with objects, features, and advantages thereof, may best be understood by reference to the following detailed description when read with the accompanying figures, in which.

It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated within the figures to indicate like elements.

DETAILED DESCRIPTION

Figures 5A, 5C:
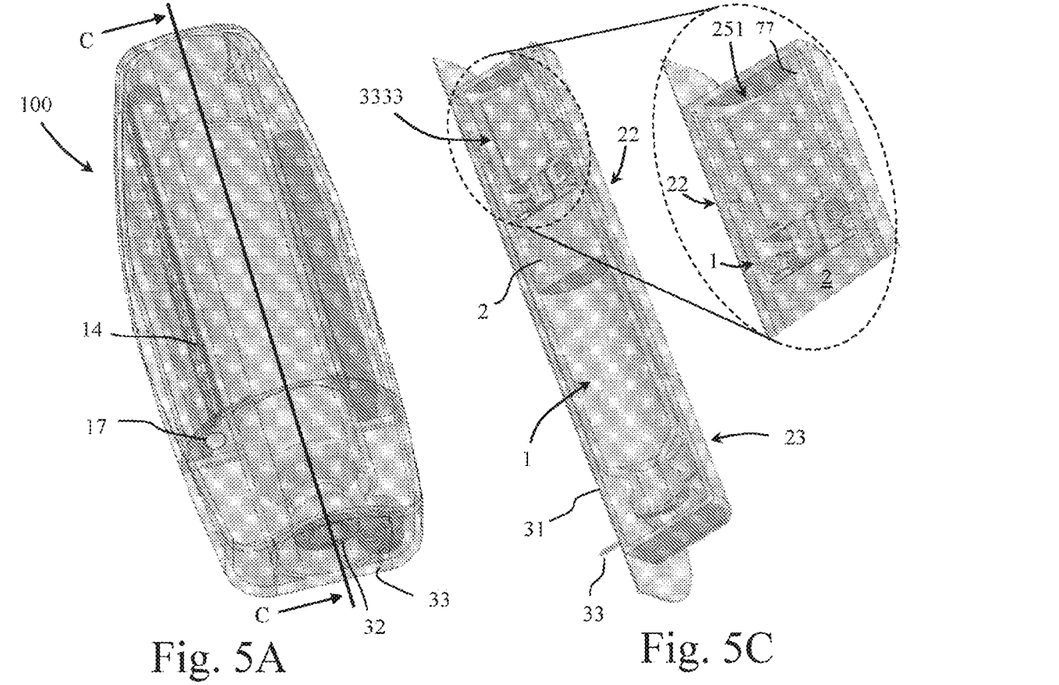
FIGS. 5A to 5C schematically show, respectively, perspective, top and cross sectional views of embodiments of a liquid delivery device of the present invention for dispensing substances.
Figure 5B:
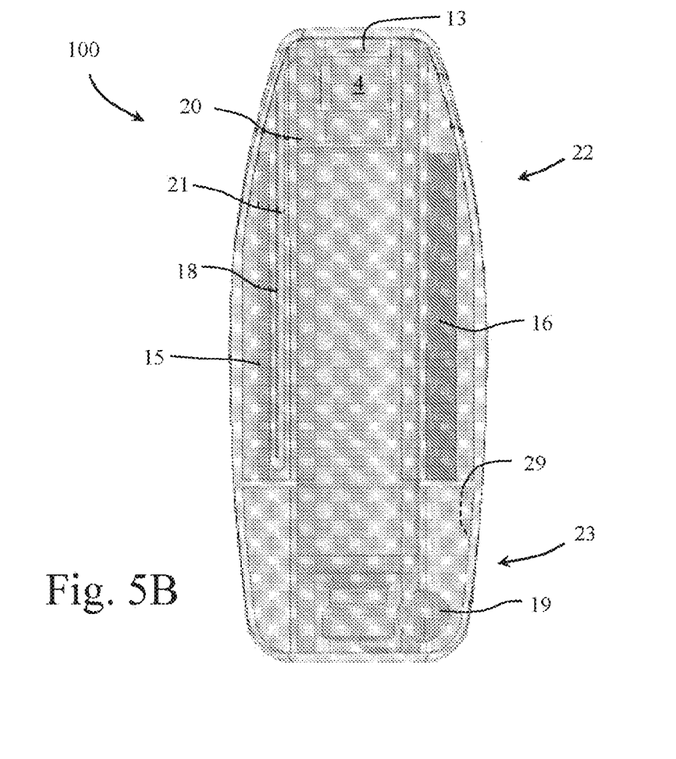

Attention is first drawn to FIGS. 5A to 5C that schematically show, respectively, perspective, top and cross sectional views of an assembled state of a liquid delivery device 100 in accordance with embodiments of the present invention. FIG. 5C is a cross sectional view of delivery device 100 as taken in plane C-C indicated in FIG. 5B.

Liquid delivery device 100 in accordance with various embodiments of the present invention may be sized and suited for delivering liquid substances, such as drugs, medications, vitamin additives, minerals, chemotherapy or chemo drugs, liquids containing DNA (or the like) to a user. In a non-binding example, such liquid substances may be insulin for assisting in regulating metabolism of carbohydrates, fats, protein (and the like) in a user of the device.

Liquid delivery device 100 may be arranged to include a rotation encoder 13 that tracks/controls rotation of a motor 4 of the crawling mechanism, a linear encoder 14 that tracks/controls linear motion of the crawling mechanism along its axis X, a PCB 15 that powers and controls electronic components used for operating the liquid delivery device, a battery 16 for powering to the liquid delivery device, a possible spring 18 that may be used for urging the crawling mechanism back towards a base position possibly within a dedicated docking site for the crawling mechanism, a seal 20 that may be located around cartridge for ingress protection, and an optional flex PCB/cable 21.

Figure 6A:
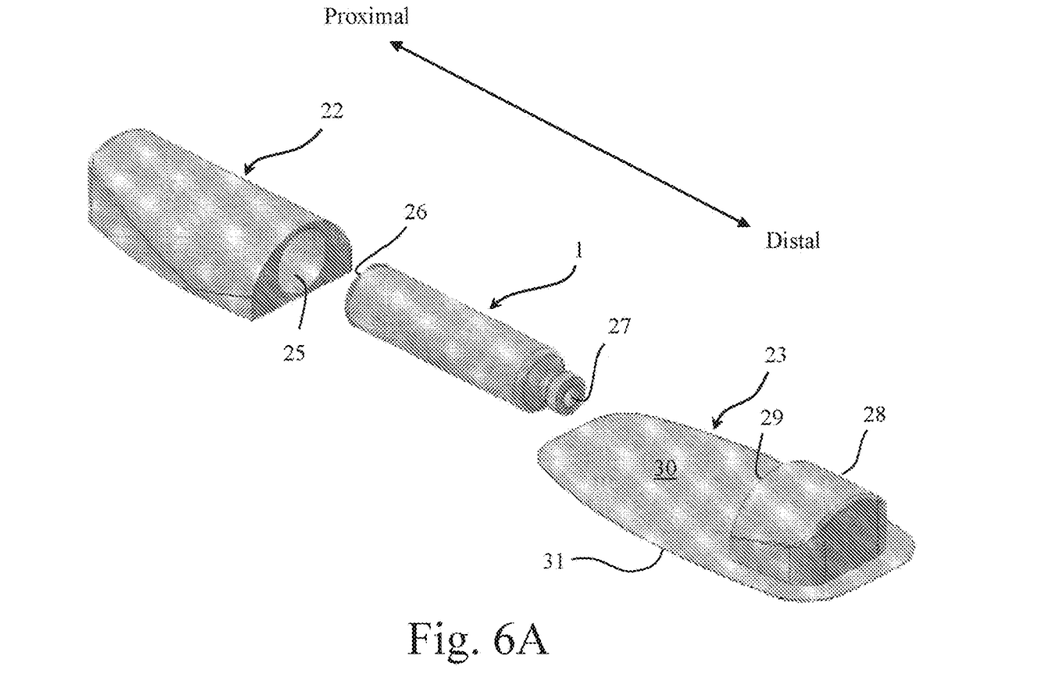
FIGS. 6A and 6B schematically show, respectively, an exploded view of the liquid delivery device seen in FIG. 5 and of another possible embodiment of a liquid delivery device slightly different to that in FIG. 5.

Delivery device 100 as seen in the disassembled state of FIG. 6A may include a reusable part 22, a replaceable cartridge 1 and a disposable part 23. Reusable part 22 as here seen includes an engagement region 25 possibly in form of a passage that opens out of the reusable part 22 at its distal side and a crawling mechanism 3333 (see FIG. 5C) that is housed within engagement region 25. The replaceable cartridge may be filled with medication and can be replaced when empty or partially empty to enable reuse of device 100.

Cartridge 1 as seen in the shown example can be formed as an elongated vessel suitable for storing liquid substances such as liquids medications, drugs, vitamin additives, minerals, chemotherapy or chemo drugs, liquids containing DNA (or the like), and may include a proximal closed side 26 and an opening 27 possibly including a septum at its distal side. In a non-binding example, such cartridge may be a type generally similar the trade named HUMALOG of Eli Lilly and Company Limited, the trade named NOVORAPID of Novo Nordisk A/S (or the like).

Disposable part 23 in this example may include a port 28 with an interior cavity 29 that opens out to a proximal side of the port, and a generally flat interface wall 30 that is adapted to contact a user of the device during its use. Interface wall 30 includes a lower face 31, possible including adhesive or the like, for attachment to a user during use of the device for dispensing liquid substance to the user.

Port 28 may be suitable for receiving a distal side of the cartridge to assume an assembled state of the liquid delivery device 100. Disposable part 23 includes liquid paths including a cannula 19 (or the like) for communication liquid substances (drugs or the like) to be administered to a user/patient.

The liquid paths within port 28 may include an upstream tip 32 suitable for entering into opening 27, possibly penetrating and/or puncturing a septum at the opening, and a downstream cannula 33 that projects away and in this view below face 31 of the interface wall in a position suitable for penetrating a skin of the user during use of the device.

Figure 6B:
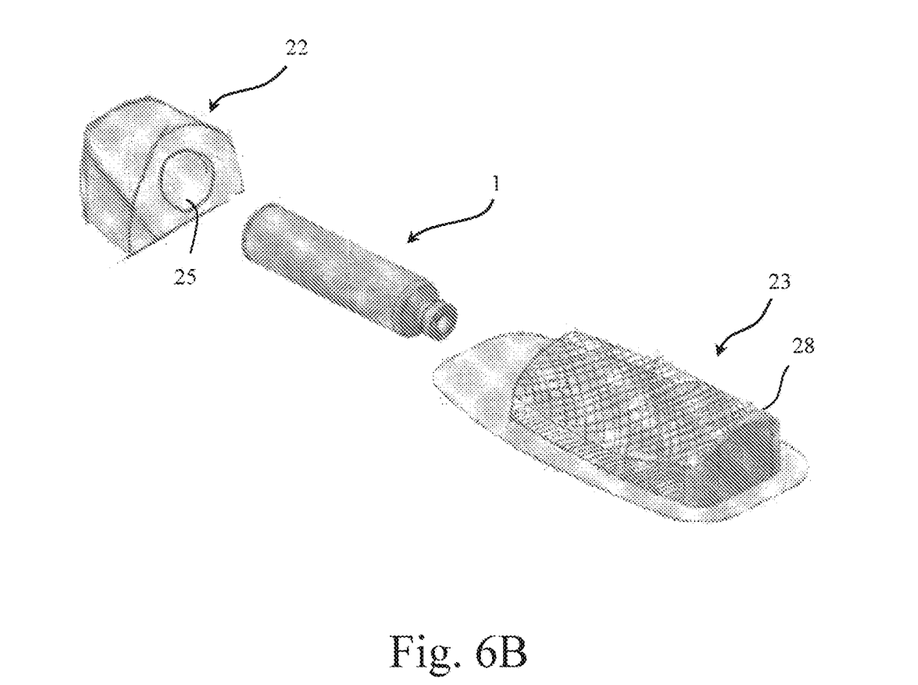

FIG. 6B schematically illustrates an embodiment of a liquid delivery device exemplifying that reusable part 22 may include engagement regions of different types for a cartridge. Engagement region 25 for example may not necessarily be formed as a passage for receiving therein a cartridge, or as shown may be formed as a shallower passage that only a portion of a cartridge may be fitted therein. Also shown in this figure is that disposable part 23 may be formed differently, e.g. to include a deeper port 28 for receiving therein the cartridge and for possibly engaging with the reusable part 22 to ensure successful assembly of the liquid delivery device.

Figure 7:
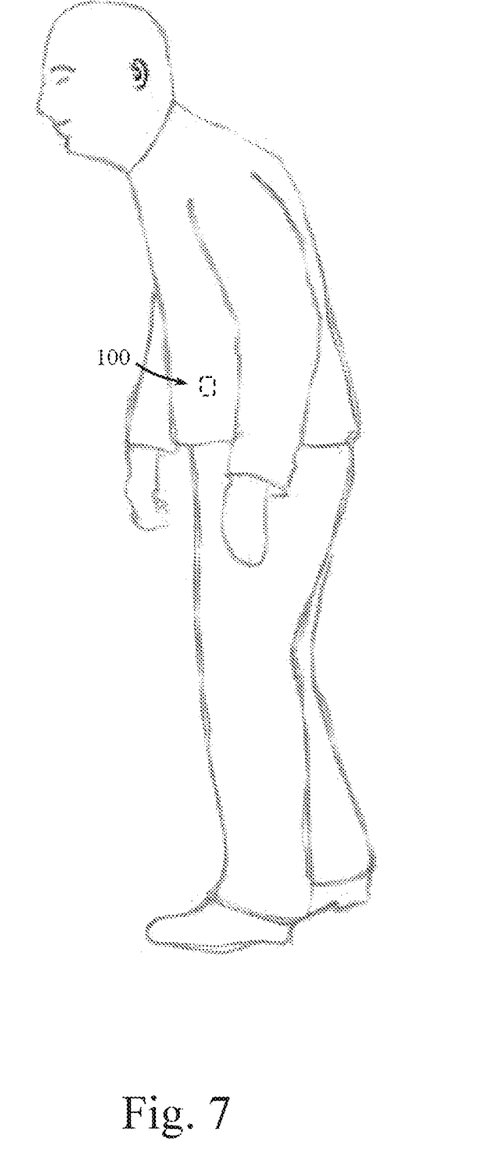
FIG. 7 schematically shows an exemplary use of a liquid delivery device in accordance with at least certain embodiments of the invention when fitted to a user of the device.
Figure 8A:
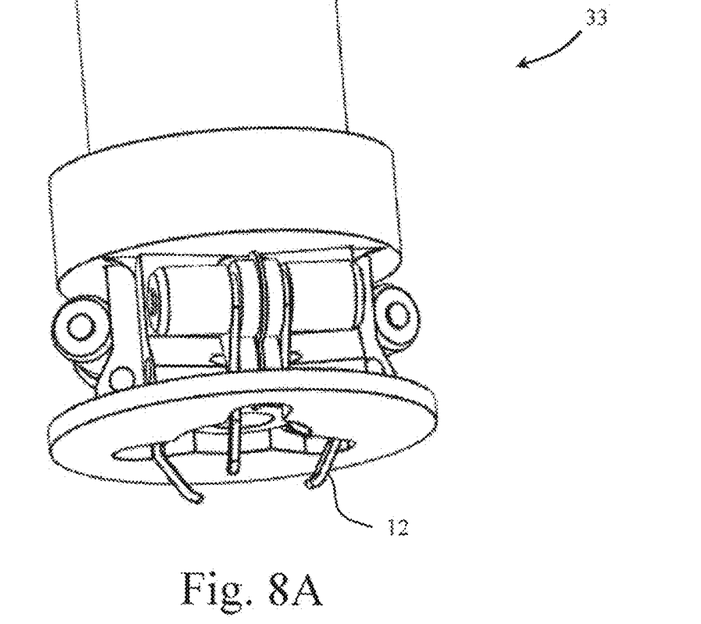
FIGS. 8A to 8D schematically show a crawling mechanism in accordance with another embodiment of the present invention during different states of operation.
Figure 8B:
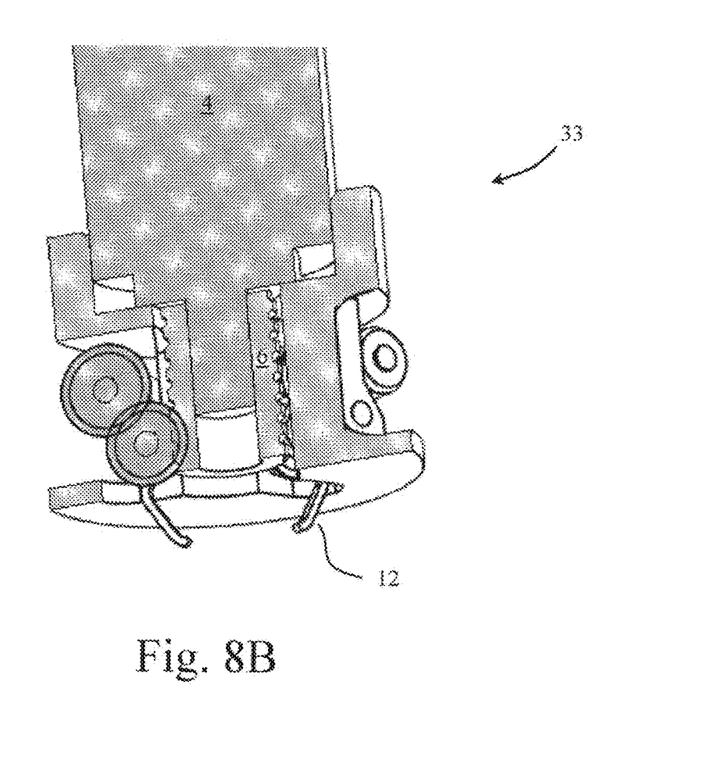
Figure 8C:
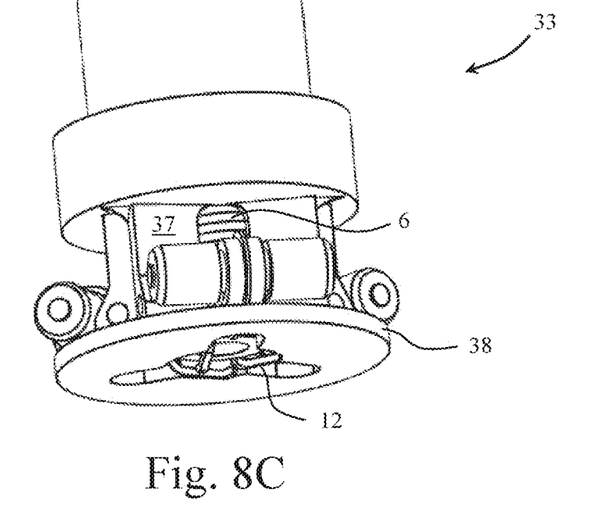
Figure 8D:
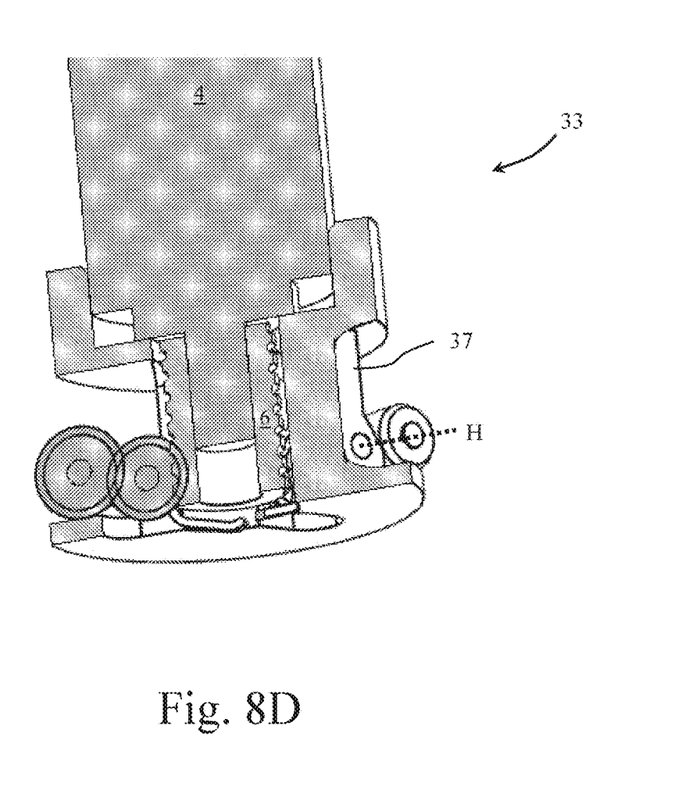
Figure 9A:
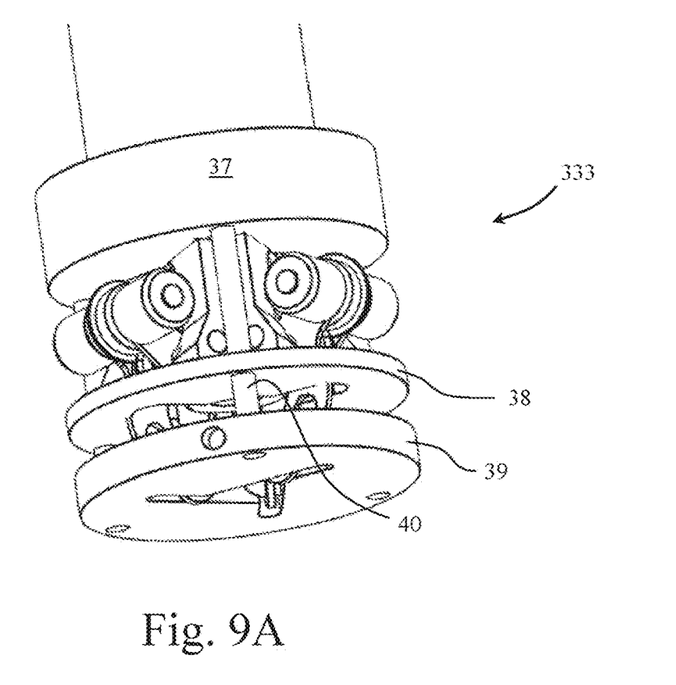
FIGS. 9A to 9D schematically show a crawling mechanism in accordance with yet another embodiment of the present invention during different states of operation.
Figure 9B:
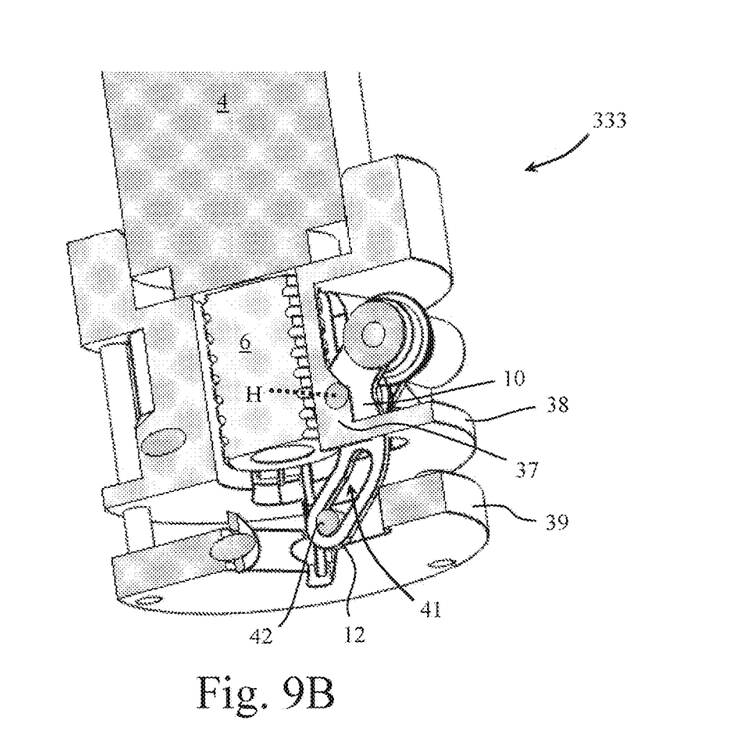
Figure 9C:
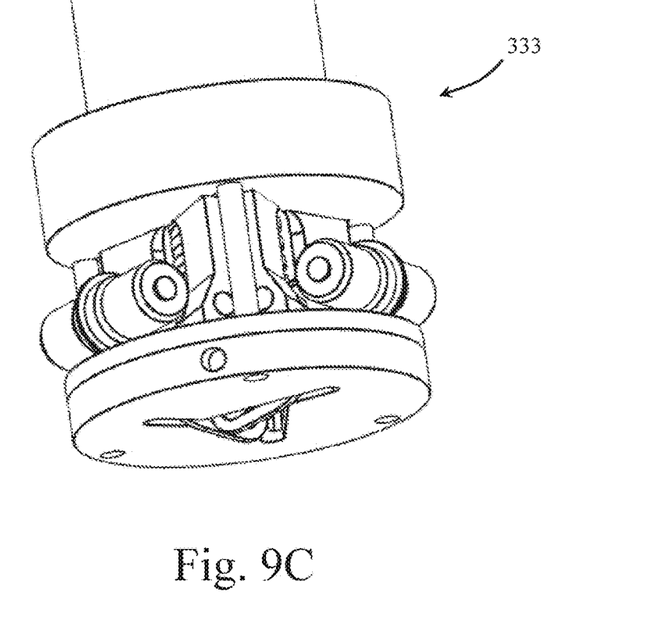
Figure 9D:
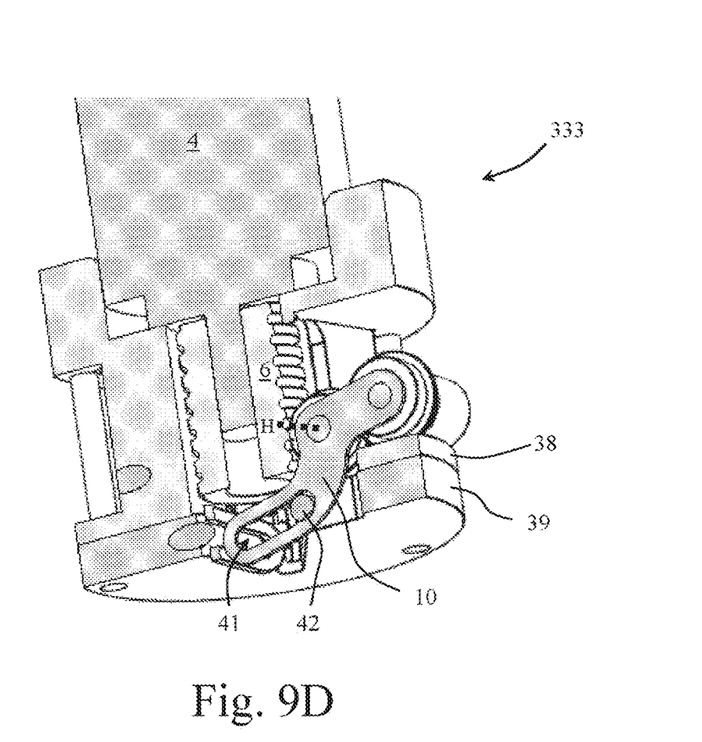

Attention is additionally drawn to FIG. 7 showing an exemplary use of a liquid delivery device 100 according to various embodiments of the invention. In this optional example, device 100 can be seen being worn on an outside of a user's body (e.g. adhered to his/her skin or attached in any other method)—here optionally around a stomach area of the user. The liquid delivery device in this example can be used for delivering various liquid substances (e.g. insulin or the like) through cannula 33, which may be placed into a layer of fat under the user's skin.

Assembly of liquid delivery device 100 may be formed by manually urging the cartridge 1 with its proximal closed side leading into engagement region 25. Cartridge 1 may be urged into engagement region 25 until it engages a distal side of the crawling mechanism 3333. Final assembly of the liquid delivery device 100 may be accomplished by placing port 28 of the disposable part over the distal side of the cartridge and then urging the disposable part 23 in a proximal direction towards the reusable part 22.

This action manually performed by a user of device 100 may result in the penetration/puncturing of opening 27 of the cartridge by upstream tip 32 and completion of insertion of the cartridge into the engagement region of the reusable part 22. A coupling sensor 17 possibly fitted to reusable part 22 and/or disposable part 23 may indicate successful assembly of the liquid delivery device 100, which includes suitable placement of the proximal side of the cartridge within engagement region 25 and the entering of upstream tip 32 into the opening at the distal side of the cartridge.

With attention drawn to FIG. 5C, cartridge 1 once suitably placed within engagement region 25 may be seen being proximal and/or substantially engaged with at its proximal side with crawling mechanism 3333. The crawling mechanism may initially be parked in a base position at a proximal region 251 of the engagement region of reusable part 22.

In the shown example in FIG. 5C, such parking of the crawling mechanism may be facilitated by provision of a docking site formation 77 formed at the proximal region 251 of the passage, which may be suitably sized to snugly receive therein the crawling mechanism at its base position, while substantially maintaining a central longitudinal axis of the crawling mechanism generally aligned with an axis of the engagement region (e.g. passage) within the reusable part and hence with a longitudinal axis of a cartridge engaged with the reusable part. Also seen in FIG. 5C is that a proximal end of cartridge 1 may optionally substantially engage with docking site 77 (that in this example has a peripheral sleeve-like formation) when suitably engaged with engagement region 25.

In the description herein below, various embodiments of crawling mechanism 3333 will be described each including/emphasizing various features/aspects that may be combinable one with the other.

Figure 1:
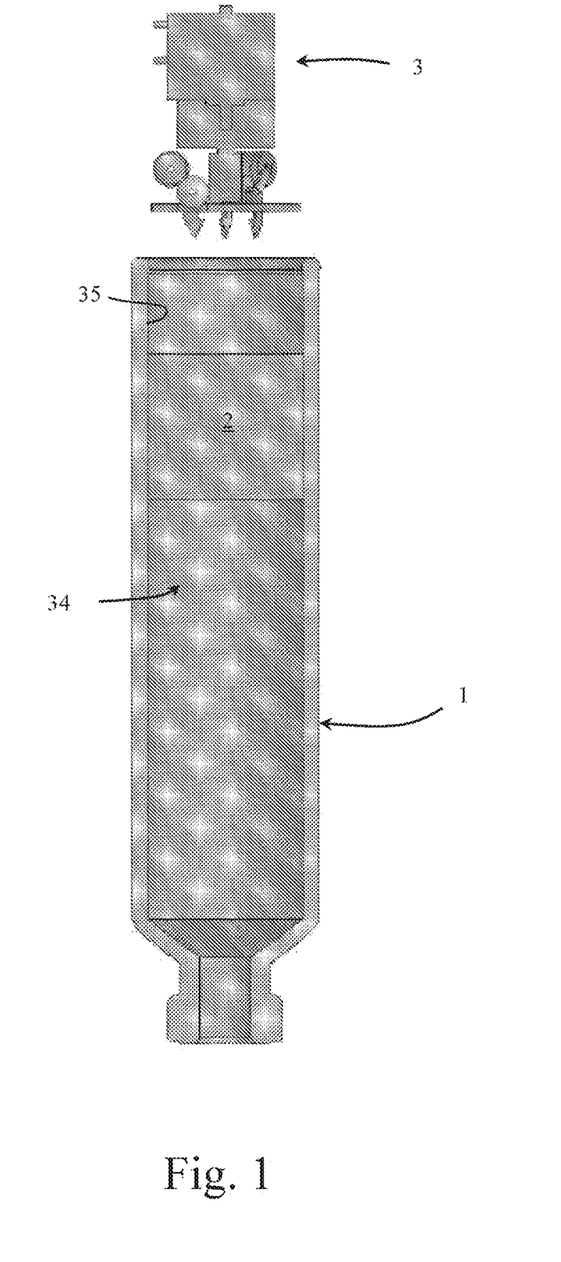
FIG. 1 schematically shows an embodiment of a portion of liquid delivery device according to the present invention exhibiting a cartridge and an embodiment of a crawling mechanism of the present invention prior to its introduction into the cartridge.

Attention is drawn to FIG. 1 to show an embodiment of a crawling mechanism 3 and a cartridge 1 prior to engagement between the two. This relative position between the crawling mechanism 3 and cartridge 1 may be representative of an initial non-final position of the cartridge within an engagement region of a reusable part 22 (engagement region of reusable part not seen in this figure).

Cartridge 1 may be seen including an interior lumen 34 and a movable plunger 2 that is located within lumen 34. Interior lumen 34 includes an inner wall 35 of cartridge 1, also referred to herein as a peripheral wall 35 of the interior lumen 34. A plunger 2 forms a proximal boundary for liquid substances located within the lumen of the cartridge, in a region of the lumen distally upstream to the plunger.

Figure 2:
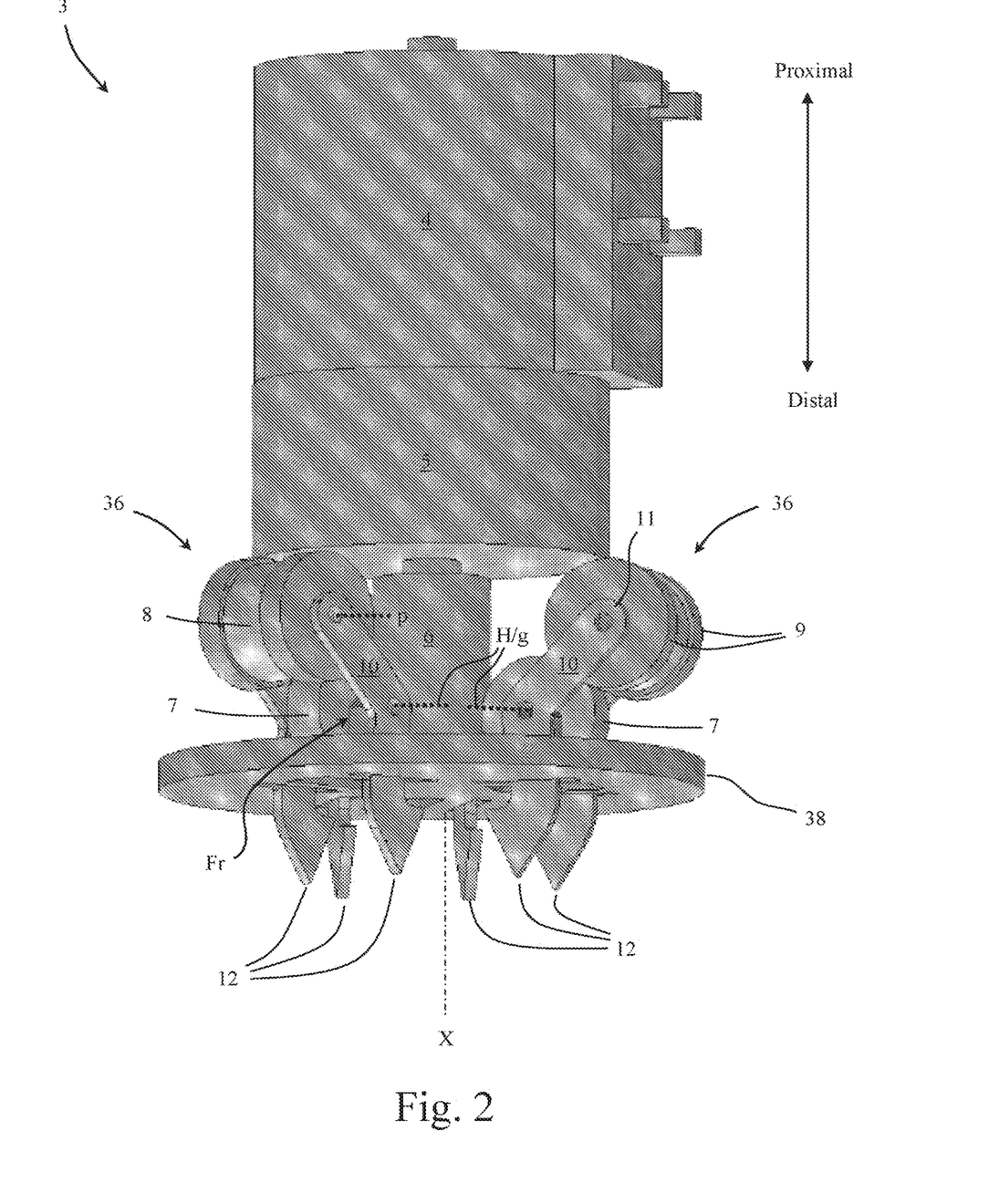
FIG. 2 schematically shows an embodiment of a crawling mechanism.

Attention is drawn to FIG. 2 for a closer view of crawling mechanism 3. Crawling mechanism 3 as seen in this example is formed along a central longitudinal axis X that defines opposing axial proximal and distal directions.

The crawling mechanism may be arranged to include a motor 4, possibly axially coupled via a gear 5 (possibly reduction gear) to a gear arrangement 6 possibly in the form of a worm drive. Activation of motor 4 may thus urge rotation of gear arrangement 6 about axis X. Crawling mechanism 3 includes a housing 37 with portions generally formed about axis X. The housing is not visible in FIG. 2 however can be seen e.g. in the crawling mechanism embodiments 33, 333 shown in FIGS. 8 and 9.

Crawling mechanism 3 includes in addition one or more swing members 36, and in the case of existence of more than one swing member such members may possibly be symmetrically distributed about axis X. In this example, the crawling mechanism 3 includes three such swing members. Each swing member 36 may include first and second gears 7, 8 that are both coupled in this example to a pair of side bars 10.

The pair of side bars 10 in each swing member 36 may be hinged to the housing so that they can pivot relative to the housing about a respective hinge axis H that is perpendicular to axis X, as indicated in FIG. 2.

Pivoting of a swing member about a hinge axis H according to the various embodiments of the present invention— may be between a starting position (see. e.g., FIGS. 3, 8A, 8B, 9A, 9B) and a terminal position (see, e.g., FIGS. 4, 8C, 8D, 9C, 9D).

In the starting position, the second gear 8 may be arranged to be generally closer to axis X of the crawling mechanism and hence displaced from a peripheral wall of a cartridge. In the terminal position, the second gear 8 may be arranged to be generally further away from axis X of the crawling mechanism and hence in a position where the one or more driving wheels 9 associated therewith may be arranged to contact a peripheral wall of a cartridge engaged therewith, preferably pressing against such peripheral wall.

Each side bar 10 extends between first 12 and second 11 ends, and each pair of side bars 10 of a respective swing member may accordingly be adapted to be pivotally coupled to the housing of the crawling mechanism about the hinge H of the respective swing member.

The first gear 7 may be coupled to the pair of side bars 10 of its swing member so that its rotational axis 'g' may be generally aligned with the hinge axis H of its swing member. The second gear 8 may be pivotally coupled about a pivot axis 'p' to the pair of side bars 10 of its swing member adjacent the second ends 11 of the side bars.

Each second gear 8 may be adapted to be fitted to rotate about its respective axis 'p' with one or more driving wheels 9 preferably of larger diameter. In this example, each second gear 8 may be sandwiched between two driving wheels 9 that are adapted to rotate together therewith about axis 'p'.

The crawling mechanism 3 may have a primary front disk 38 located at its distal side and the ends 12 of the side bars may be adapted to project in this example in a distal direction beyond disk 38 through respective openings formed in the disk.

Figure 3:
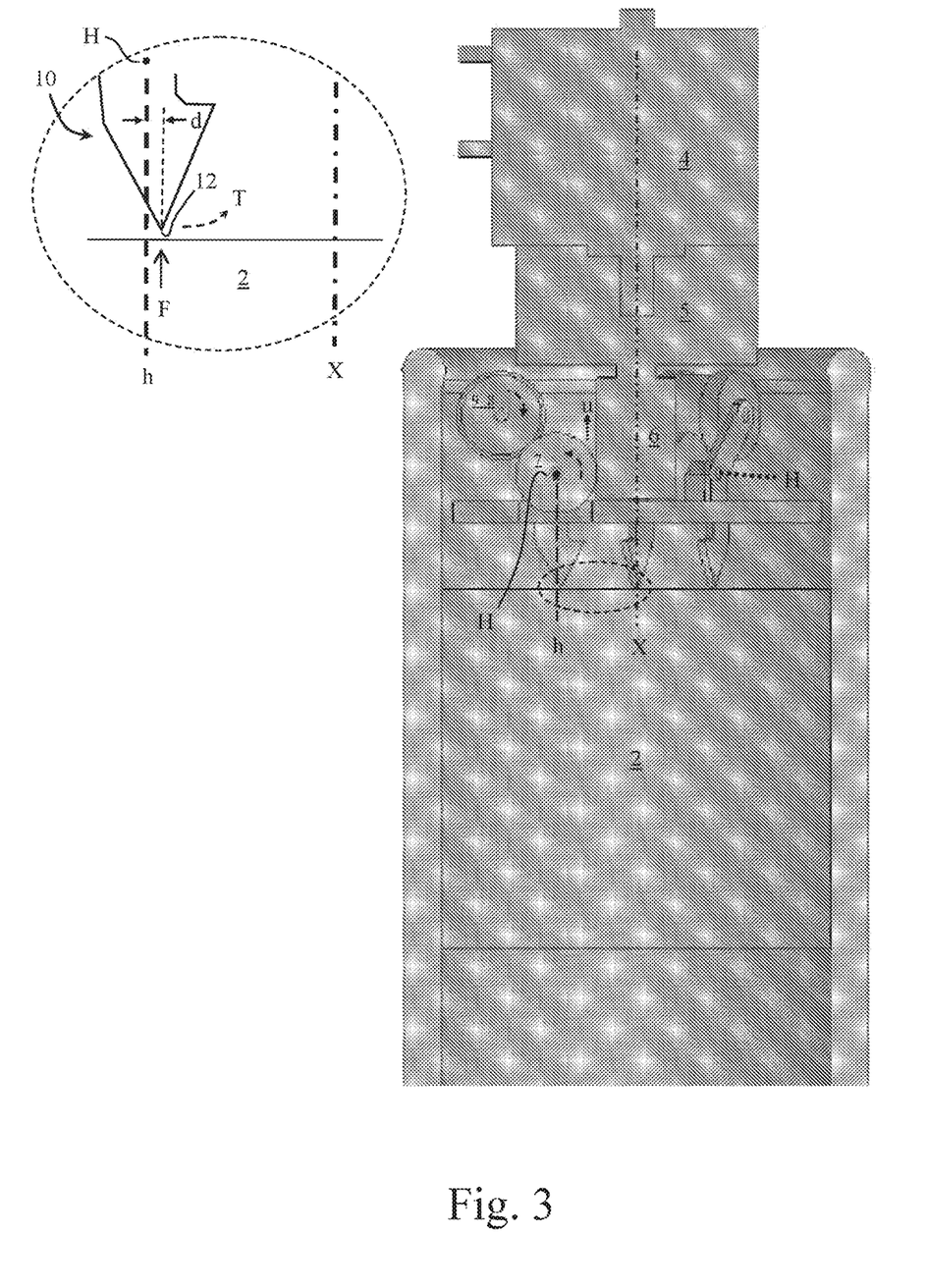
FIG. 3 schematically shows an engagement stage between a crawling mechanism and a cartridge.

Attention is drawn to FIG. 3 illustrating a relative position of the crawling mechanism within the lumen 34 of the cartridge, where the ends 12 of the side bars of the crawling mechanism are generally adjacently abutting plunger 2 of the cartridge. This relative location between the cartridge/plunger and the crawling mechanism may be obtained while a user pushes the cartridge in a proximal direction into the engagement region 25 of the reusable part 22. The swing members of the crawling mechanism are located in this view generally in their starting positions.

In an aspect of the preset invention, crawling mechanisms of various embodiments of the invention may be designed to urge their swing member(s) during use to swing about their respective hinge axes H between the starting and terminal positions.

Swinging about a hinge axis H towards the terminal position may be activated e.g. when advancing to administer liquid substances out of the cartridge and may be controlled by triggering motor to rotate in a first rotational direction. Swinging about a hinge axis H towards the starting position may be activated e.g. after completion of use of a cartridge to assist in disengaging the crawling mechanism from the cartridge and may be controlled by triggering motor to rotate in a second rotational direction that opposes the first rotational direction.

With attention drawn to the enlarged view in FIG. 3, design characteristics that may assist in the urging of a swing member about its hinge axis H can be observed.

In this enlarged view a plane 'h' that includes a hinge H of a given one of the swing members of the crawling mechanism is indicated together with the central axis X of the crawling mechanism. Plane 'h' is substantially parallel to axis X.

Also marked in this enlarged view is a position of an end 12 of a side bar of the given swing member relative to plane 'h' and axis X. As seen, in the starting position of the swing member, an end 12 of the side bar of such swing member may be designed to be located on an inner side of plane 'h' that is closer to axis X— here shifted by a distance 'd' towards axis X.

As a result of such positioning of the ends 12 of the side bars, as cartridge is urged by a user of the device to a position more proximal within the passage of the reusable part 22, and reaches a position where the plunger 2 of the cartridge starts to engage with the ends 12 of the bars, any continued proximal movement of the cartridge may form a force F that is applied upon the ends 12 of the side bars—that in turn may urge formation of a torque T that is applied upon the side bars in a direction indicated by the dashed arrow in the enlarged section of FIG. 3.

Figure 4:
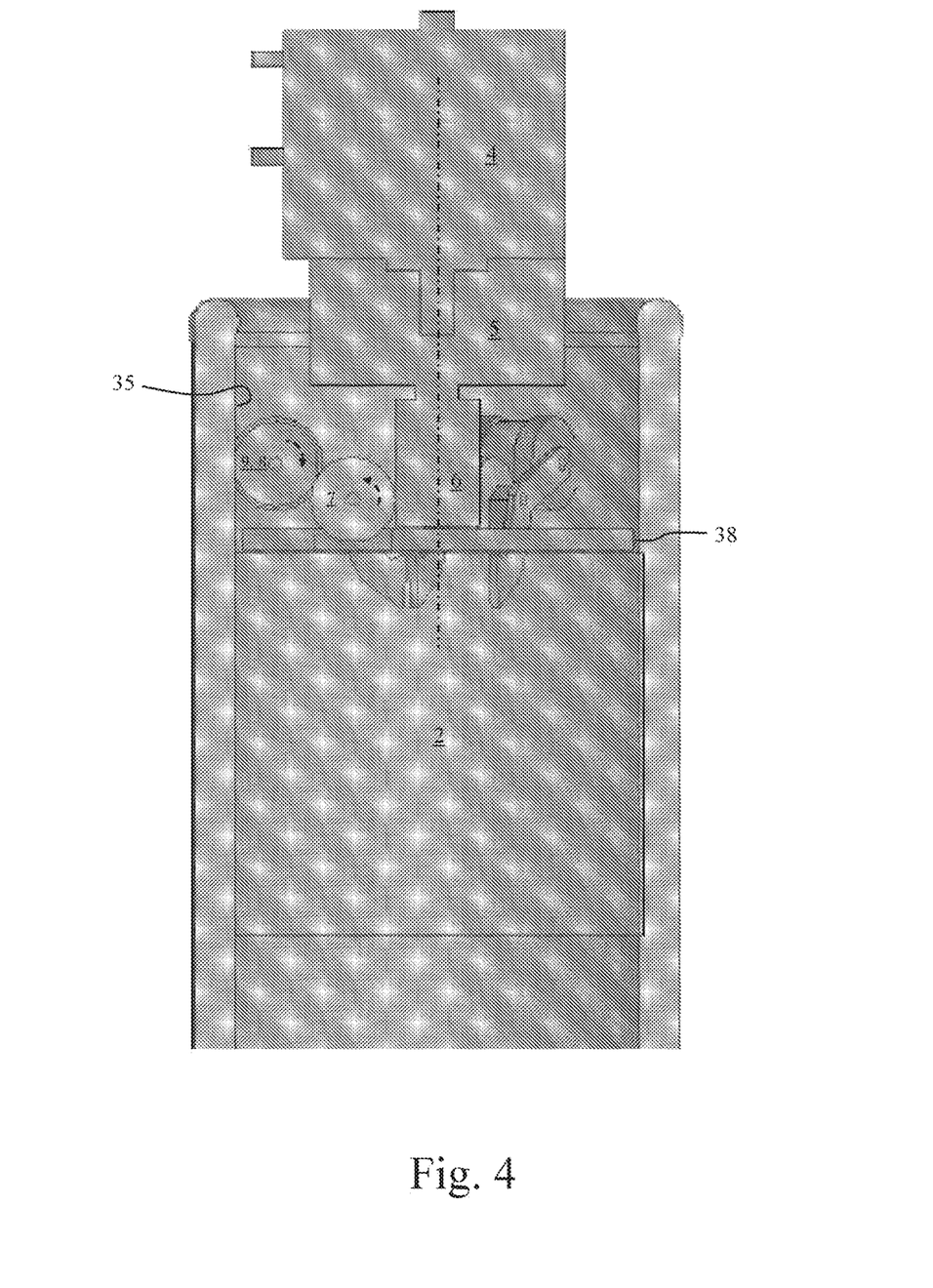
FIG. 4 schematically shows a further engagement stage between a crawling mechanism and a cartridge.

Such torque forces T acting upon the side bars of a crawling mechanism are adapted to swing each swing member 36 about its respective hinge H towards its terminal position in a direction that urges the second gear 8 and consequently the one or more driving wheels 9 associated therewith towards contact with the peripheral wall 35 of lumen 34 of the cartridge as seen in FIG. 4.

With attention drawn to the main view in FIG. 3, an additional mechanism aimed at urging the swing members of a crawling mechanism to swing about their hinge axes H can be seen. This mechanism may be activated by motor 4 of the crawling mechanism. Upon activation of the motor e.g. in a direction aimed at urging crawling mechanism to move in a distal direction relative to the cartridge, to thus administer liquid substances out the of the cartridge, gear arrangement 6 may be adapted to rotate in a direction that imparts an upwardly directed force 'u' upon the first gear 7 of each swing member.

This upwardly directed force 'u' indicated in FIG. 3 by the upwardly pointed dotted arrow, in turn urges the first gear 7 of each swing member to rotate in a first rotational direction, which in turn urges the second gear 8 of each swing member to rotate in a second opposing rotational direction—so that when the second gear 8 may be engaged via the one or more driving wheels 9 with a peripheral wall 35 of a cartridge lumen, the crawling mechanism may be urged to move relative to the cartridge in a distal direction.

This additional mechanism aimed at urging the swing members of a crawling mechanism to swing about their hinge axes H may thus be assisted by the upwardly or downwardly directed forces applied by the gear arrangement 6 upon the first gear 7 of each swing member.

An upwardly directed force 'u' as seen in FIG. 3 urging rotation of first gear 7 may assist in rotating the swing members towards their terminal positions due to friction (see 'Fr' indicated in FIG. 2) that is designed to occur between first gear 7 and elements of the swing member (e.g. friction caused due to ensuring that first gear 7 is pressed against at least one of the side bars or the like). An opposing downwardly directed force activated by triggering motor 4 to rotate in an opposing direction about axis X and hence urging rotation of first gear 7 in an opposing direction may assist in rotating the swing members due to said same friction 'Fr' towards their starting positions.

Thus, in at least certain embodiments—this additional mechanism aimed at urging the swing members of a crawling mechanism to swing about their hinge axes H may be seen as being arranged to occur also when the crawling mechanism is held in a position where it does not engage any other objects external to the crawling mechanism (such as the plunger of cartridge as discussed above) and thus such swinging actions may be powered by the motor alone (e.g. without any spring mechanisms or the like aimed to assisting in such swinging).

FIG. 4 indicates a position where the crawling mechanism is activated to move in the distal direction relative to the cartridge, by rotating the second gear 8 of each swing member and the one or more driving wheels 9 associated therewith to "drive" down in the distal direction along the peripheral wall 35 of a cartridge lumen.

Observing the transition of a swing member between FIGS. 3 and 4 exemplifies that in the shown embodiment, transition of a swing member from its initial position (FIG. 3) towards its terminal position (FIG. 4) is adapted to bias and move the second gear 8 and driving member 9 associated therewith from a relative proximal position towards a relative distal position where it is designed to engage with a peripheral wall 35 of a cartridge lumen to start a crawling action of the crawling mechanism.

Also seen in FIG. 4 is an optional arrangement where the ends 12 of the side bars of the swing members are suitably shaped in a hook-like formation so that they may be designed to possibly penetrate at least partially into the plunger of the cartridge. In this position primary front disk 38 may be arranged to engage against the plunger to urge it in the distal direction.

Attention is drawn to FIGS. 8A to 8D illustrating an embodiment of a crawling mechanism 33 that exemplifies side bars with ends 12 that are suited to snugly be received within the primary front disk 38 so as to substantially not project in a distal direction beyond disk 38 and by that substantially avoid penetration into the plunger of the cartridge during use. Also seen in this view is that optionally only one of the side bars includes an end 12 adapted to project in the distal direction.

Attention is drawn to FIGS. 9A to 9D illustrating an embodiment of a crawling mechanism 333 that exemplifies measures taken to ensure that all swing members are arranged to substantially pivot together between their starting and terminal positions. In this example, this may be accomplished by forming a secondary disk 39 that is located at a distal side of the primary disk 38. Secondary disk 39 can be fixed to pins 40 that pass through the primary disk and are slidingly received within the housing sleeve 37 of the crawling mechanism.

Each side bar 10 of a swing member in this crawling mechanism may include a slit 41 that in this example extends towards its end 12, and a respective shaft 42 that is adapted to pass through each slit 41 to engage each one of the side bars with the secondary disk 39. Thus relative movement between the secondary and primary disks that may be accomplished by distal or proximal axial sliding movements of the secondary disk 39 in relation to the primary disk 38 that may be kept substantially in place, may be adapted to urge coordinated similar pivoting of the swing members about their hinge axes H due to engagement between the shafts 42 and side bars as they pass along substantially similar shaped slits 41 formed within each one of the side bar.

Such coordinated pivoting of the swing members of a crawling mechanism may assist in ensuring suitable operation of the mechanism e.g. for engaging a peripheral wall of an inner lumen of the cartridge or e.g. for ensuring disengagement of a crawling mechanism from a cartridge (or the like).

In the description and claims of the present application, each of the verbs, "comprise" "include" and "have", and conjugates thereof, are used to indicate that the object or objects of the verb are not necessarily a complete listing of members, components, elements or parts of the subject or subjects of the verb.

Further more, while the present application or technology has been illustrated and described in detail in the drawings and foregoing description, such illustration and description are to be considered illustrative or exemplary and non-restrictive; the technology is thus not limited to the disclosed embodiments. Variations to the disclosed embodiments can be understood and effected by those skilled in the art and practicing the claimed technology, from a study of the drawings, the technology, and the appended claims.

In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measures can not be used to advantage.

The present technology is also understood to encompass the exact terms, features, numerical values or ranges etc., if in here such terms, features, numerical values or ranges etc. are referred to in connection with terms such as "about, ca., substantially, generally, at least" etc. In other words, "about 3" shall also comprise "3" or "substantially perpendicular" shall also comprise "perpendicular". Any reference signs in the claims should not be considered as limiting the scope.

Although the present embodiments have been described to a certain degree of particularity, it should be understood that various alterations and modifications could be made without departing from the scope of the invention as hereinafter claimed.

The invention claimed is:

1. A crawling mechanism for driving a plunger of a cartridge in a liquid delivery device, the crawling mechanism having a central longitudinal axis and being arranged to crawl in an axial direction, the crawling mechanism comprising:
    a housing;
    a motor; and
    one or more swing members pivotally coupled to the housing, wherein each of the one or more swing members is arranged to swing relative to the housing between an initial position and a terminal position, at which a driving wheel of the swing member is in contact with the an inner wall of the cartridge and at which a torque generated by the motor is transferred to the driving wheel, rotating the driving wheel along the inner wall to move the crawling mechanism in a forward movement that moves the plunger to eject a liquid from the cartridge.

2. The crawling mechanism of claim 1, wherein swing member pivots relative to the housing about a respective hinge axis that is perpendicular to the central longitudinal axis.

3. The crawling mechanism of claim 1, wherein the one or more swing members are two or more swing members, symmetrically distributed about the central longitudinal axis.

4. The crawling mechanism of claim 1, wherein each swing member comprises a gear arrangement and wherein the torque generated by the motor rotates the gears arrangement to urge transition of the swing member between the initial and terminal positions.

5. The crawling mechanism of claim 4, wherein the torque is generated by the motor operating in a first rotational direction and wherein operation of the motor in an opposing second rotational direction detaches the driving wheel from the inner wall of the cartridge.

6. The crawling mechanism of claim 1, wherein the one or more swing members are multiple swing members, wherein each swing member comprises a gear arrangement, wherein the torque generated by the motor rotates the gear arrangement to swing the swing member between the initial and terminal positions, and vice versa, and wherein swinging of all the swing members is synchronized to occur substantially simultaneously.

7. A drug delivery device comprising:
a crawling mechanism for driving a plunger of a cartridge engaged in the drug delivery device, the crawling mechanism having a central longitudinal axis and comprising a housing, a motor, and one or more swing members pivotally coupled to the housing, wherein each of the one or more swing members is arranged to swing relative to the housing between an initial position and a terminal position at which a driving wheel of the swing member is in contact with an inner wall of the cartridge and at which a torque generated by the motor is transferred to the driving wheel, rotating the driving wheel along the inner wall to move the crawling mechanism in a forward direction that moves the plunger to eject a liquid from the cartridge;
a reusable part for engaging the cartridge with the crawling mechanism; and
a disposable part placed on the cartridge when engaged with the reusable part.

8. The drug delivery device of claim 7, wherein the disposable part further comprises a cannula for releasing the liquid directly to a user.

9. The drug delivery device of claim 8, and further comprising an adhesive to attach the drug delivery device onto a body region of the user.

10. The drug delivery device of claim 7, wherein the reusable part includes a docking site for receiving the crawling mechanism and aligning the crawling mechanism to engage the cartridge.

11. The drug delivery device of claim 10, further comprising an elastic element arranged to pull the crawling mechanism into the docking site when the driving wheel pivots away from the wall of the cartridge.

12. The drug delivery device of claim 7, further comprising a coupling sensor triggering detachment of the driving wheel when the disposable part is detached from the reusable part.

13. The drug delivery device of claim 7 and further comprising an encoder for tracking linear motion of the crawling mechanism in the direction of the central longitudinal axis.

14. A method for delivering a liquid comprising
providing a drug delivery device comprising a disposable part, a reusable part, a replaceable cartridge engaged with the reusable part, and a crawling mechanism housed within the reusable part, the crawling mechanism having a central longitudinal axis and comprising a housing, a motor, and one or more swing members pivotally coupled to the housing, wherein each of the one or more swing members is arranged to swing relative to the housing between an initial position and a terminal position at which a driving wheel of the swing member is in contact with an inner wall of the cartridge and at which a torque generated by the motor is transferred to the driving wheel, rotating the driving wheel along the inner wall to move the crawling mechanism in a forward direction that moves the plunger to eject a liquid from the cartridge.

15. The method of claim 14, wherein the torque of the motor is in a first rotational direction, and wherein an opposing torque of the motor in an opposing second rotational direction is adapted to detach the driving wheel from the inner wall of the cartridge.

16. The method of claim 15, wherein once the driving wheel is separated from the cartridge, an elastic element is arranged to pull the crawling mechanism back in a proximal direction, towards a docking site within the reusable part.

* * * * *